(12) United States Patent
Hinks et al.

(10) Patent No.: US 8,483,457 B2
(45) Date of Patent: Jul. 9, 2013

(54) SYSTEM AND METHOD OF IMAGE ARTIFACT REDUCTION USING SELF-NAVIGATED REAL-TIME PHASE CORRECTION IN ECHO PLANAR IMAGING

(75) Inventors: Richard Scott Hinks, Waukesha, WI (US); Dan Xu, Oconomowoc, WI (US)

(73) Assignee: General Electric Company, Schenectady, NY (US)

( * ) Notice: Subject to any disclaimer, the term of this patent is extended or adjusted under 35 U.S.C. 154(b) by 472 days.

(21) Appl. No.: 12/831,562

(22) Filed: Jul. 7, 2010

(65) Prior Publication Data

US 2012/0008842 A1 Jan. 12, 2012

(51) Int. Cl.
*G06K 9/00* (2006.01)
(52) U.S. Cl.
USPC .......................................................... 382/128
(58) Field of Classification Search
USPC .......................................................... 382/128
See application file for complete search history.

(56) References Cited

U.S. PATENT DOCUMENTS

| 6,341,179 | B1 * | 1/2002 | Stoyle et al. | 382/254 |
|---|---|---|---|---|
| 7,102,352 | B2 | 9/2006 | Hinks et al. | |
| 7,259,557 | B2 | 8/2007 | Hinks et al. | |
| 7,860,291 | B2 * | 12/2010 | Hwang | 382/131 |
| 7,945,305 | B2 * | 5/2011 | Aggarwal et al. | 600/413 |
| 8,310,233 | B2 * | 11/2012 | Trzasko et al. | 324/309 |
| 2004/0071324 | A1 * | 4/2004 | Norris et al. | 382/128 |
| 2005/0253580 | A1 * | 11/2005 | Huang et al. | 324/307 |
| 2008/0310696 | A1 * | 12/2008 | Hwang | 382/131 |
| 2010/0085049 | A1 * | 4/2010 | Park et al. | 324/309 |

\* cited by examiner

*Primary Examiner* — Sheetal R Rangrej
(74) *Attorney, Agent, or Firm* — Ziolkowski Patent Solutions Group, SC

(57) ABSTRACT

An apparatus and method include a computer programmed to implement a scan sequence configured to elicit scan data, wherein the scan sequence comprises an echo planar imaging (EPI) sequence configured to elicit the image data and to acquire the scan data. The computer is also programmed to manipulate the scan data to determine a first plurality of phase errors in the image data responsible for a Nyquist ghost, wherein the manipulated scan data is free of navigator echo data, remove the first plurality of phase errors from the image data, and reconstruct an image based on the image data having the first plurality of phase errors removed therefrom.

20 Claims, 2 Drawing Sheets

SYSTEM AND METHOD OF IMAGE ARTIFACT REDUCTION USING SELF-NAVIGATED REAL-TIME PHASE CORRECTION IN ECHO PLANAR IMAGING

BACKGROUND OF THE INVENTION

Embodiments of the invention relate generally to magnetic resonance (MR) imaging and, more particularly, to minimizing phase errors in MR imaging data.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_Z$, may be rotated, or "tipped", into the x-y plane to produce a net transverse magnetic moment $M_t$. As appreciated by those skilled in the art, one or more radio-frequency (RF) pulses are generally employed to create the excitation field, $B_1$, which is applied to the substance or tissue, thus manipulating an ensemble of spins thereof.

After application of the $B_1$ excitation field, a signal emitted by the ensemble of spins is acquired and processed to form an image. Depending on the technique employed, the ensemble of spins may be subjected intervening acts prior to acquisition of the image signal. There are a variety of imaging techniques employed in the MR setting.

For example, echo planar imaging (EPI) is a fast imaging technique often used in the field of MR imaging. Generally, during the implementation of an EPI technique, an entire 2D k-space data set is acquired using one or more "shots," where each shot typically acquires multiple k-space lines by a sequence of readout gradients with alternating polarities. EPI generates "snapshot" images and has been employed with various MR imaging applications, including diffusion weighted imaging and functional MR imaging (fMRI).

EPI techniques, however, can be affected by several drawbacks. For example, due to the readout gradients having alternating polarities, typically every second line of data is traversed backward in the k-space. Accordingly, such data is typically time-reversed before a Fourier transform is applied thereto. The fact that there is almost always asymmetric modulation corrupting the MR signal (due to eddy current, receiver filter asymmetry, concomitant field etc.) and the need to time-reverse every other echo leads to alternating signal modulation between even and odd echoes, which results in the well-known Nyquist ghost artifact. Another example of the drawbacks in EPI is the shifting of an imaged object over several images taken at different time points due to the drifting $B_0$ field.

Hardware improvement and pre-compensation (e.g., gradient pre-emphasis to reduce eddy current) can be employed to reduce the effects of ghost artifacts such as the Nyquist ghost artifact. Nevertheless, one or more ghost correction methods are still required during image reconstruction to further reduce the Nyquist ghost to an acceptable level when an EPI technique is employed. Such correction methods are typically called phase correction methods as they correct or minimize phase modulation or errors along the readout, which is usually the dominant term over magnitude modulation.

One common phase correction method collects non-phase-encoded reference data via a reference scan before collecting imaging data via an imaging scan. Using the non-phase-encoded reference data, a phase difference (i.e., static modulation) between even and odd echoes can be determined. To minimize Nyquist ghosting artifacts, this phase difference is removed from imaging data collected via the subsequent imaging scan. This type of phase correction method is often used in static EPI, where EPI images of a single time point are acquired following the reference scan.

Other correction methods may be used when the EPI technique employed is a dynamic EPI technique, such as fMRI, where a time series of EPI images are collected. Often, dynamic EPI techniques generate additional modulation along readout due to factors such as temperature-related drift, thereby resulting in an increase of ghost level over time (i.e., ghost drift). Typically, the phase correction method discussed above with respect to static EPI cannot account for such additional modulation. To address this ghost drift problem, often a navigator-based correction method is employed. For example, non-phase-encoded navigator echoes can be collected with the EPI data at each temporal frame to calibrate the additional modulation between odd and even echoes. Using navigator echo data, which is elicited by navigator echo pulses, the per-temporal-frame modulation can be corrected during image reconstruction. If a non-phase-encoded reference scan is also employed, static modulation measured from the reference scan can also be corrected during the image reconstruction.

With regard to the navigator echoes, navigator echo pulses are typically incorporated into the scan echo train as its first few echoes (e.g., 3-6 echoes) primarily for signal to noise ratio (SNR) consideration. The navigator-based correction method, however, can have drawbacks. For example, navigator echoes typically prolong the echo train and therefore reduce the maximum number of slices per repetition time (TR). More importantly, it assumes that the additional modulation that the center echoes (corresponding to echoes covering the center of the k-space, which contribute to majority of the signal energy) experience is the same as that predicted by the navigator echoes. When this assumption is not true, the modulation of the center echoes will not be well corrected, thereby still leading to significant drift of the Nyquist ghost.

It would therefore be desirable to provide an apparatus and method to minimize at least Nyquist ghosting in EPI.

BRIEF DESCRIPTION OF THE INVENTION

In accordance with one aspect of the invention, a magnetic resonance imaging (MRI) apparatus includes an MRI system having a plurality of gradient coils positioned about a bore of a magnet, and a radio-frequency (RF) transceiver system and an RF switch controlled by a pulse module to transmit RF signals to an RF coil assembly to acquire MR images. The MRI apparatus also includes a computer programmed to implement a scan sequence configured to elicit scan data, wherein the scan sequence comprises an echo planar imaging (EPI) sequence configured to elicit the image data and to acquire the scan data. The computer is also programmed to manipulate the scan data to determine a first plurality of phase errors in the image data responsible for a Nyquist ghost, wherein the manipulated scan data is free of navigator echo data, remove the first plurality of phase errors from the image data, and reconstruct an image based on the image data having the first plurality of phase errors removed therefrom.

According to another aspect of the invention, a method a method of magnetic resonance (MR) imaging includes acquiring MR data with at least one MR coil, wherein the MR data comprises echo planar imaging (EPI) data and determining a first set of coefficients for phase correction from the EPI data, wherein determining the first set of coefficients does not rely on navigator echo data. The method also includes employing the first set of coefficients to remove Nyquist ghosting phase errors in the EPI data and reconstructing a plurality of images from the EPI data having the Nyquist ghosting phase errors removed therefrom.

According to another aspect of the invention, a computer readable storage medium having a sequence of instructions stored thereon, which, when executed by a computer, causes the computer to initiate a magnetic resonance (MR) scan that employs an echo planar imaging (EPI) sequence configured to elicit imaging data and to determine a first set of phase correction coefficients from the imaging data, wherein the determination of the first set of phase correction coefficients does not rely on navigator echo data. The instructions also cause the computer to employ the first set of phase correction coefficients to remove a first set of phase errors from the imaging data responsible for Nyquist ghosting and to reconstruct at least one image from the imaging data having the first set of phase errors removed.

Various other features and advantages will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION

Figure 1:
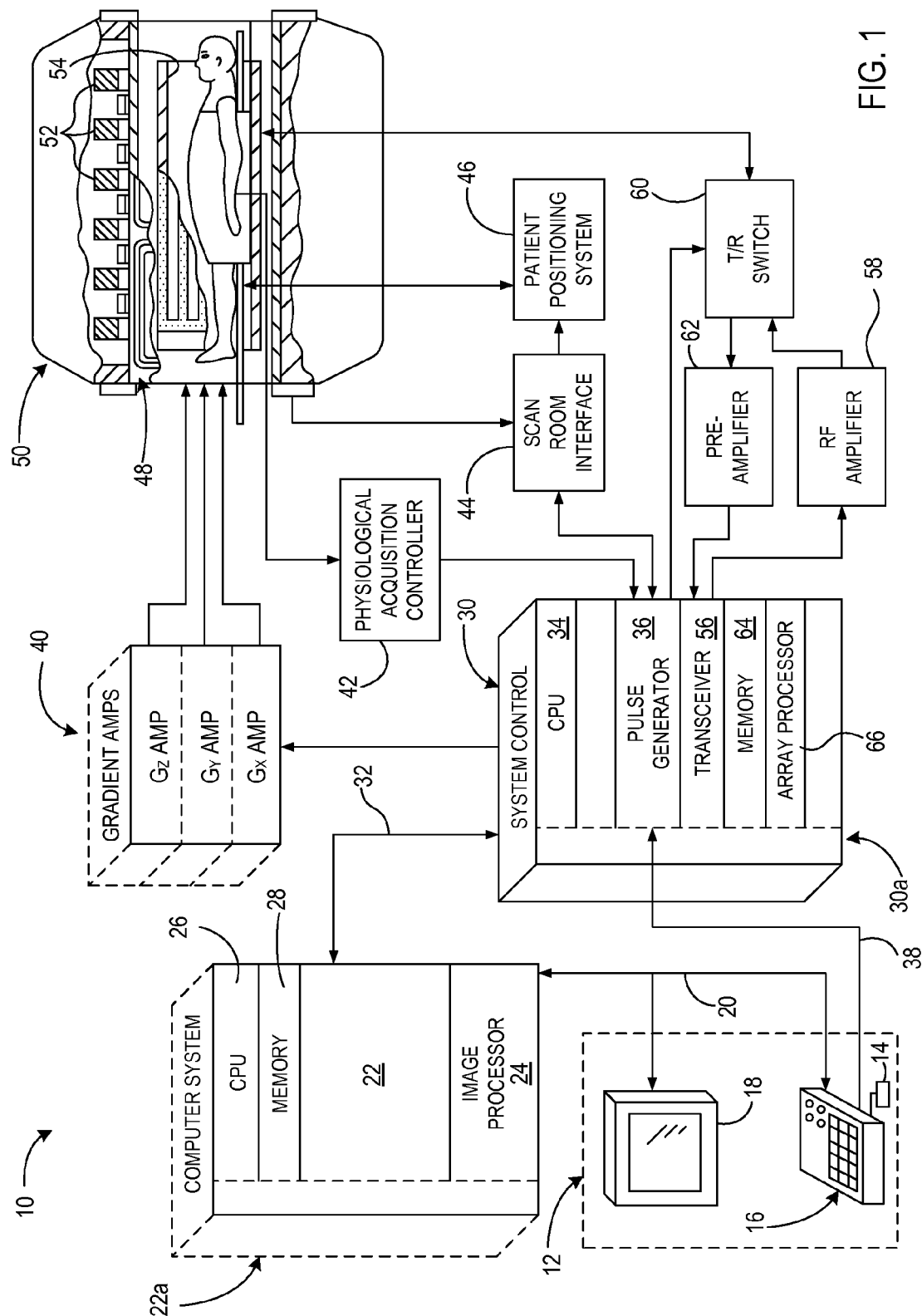
FIG. 1 is a block diagram of an MR system according to an embodiment of the invention.

Referring to FIG. 1, the major components of a preferred magnetic resonance imaging (MRI) system 10 incorporating an embodiment of the invention are shown. The operation of the system is controlled from an operator console 12 which includes a keyboard or other input device 14, a control panel 16, and a display screen 18. The console 12 communicates through a link 20 with a separate computer system 22 that enables an operator to control the production and display of images on the display screen 18. The computer system 22 includes a number of modules which communicate with each other through a backplane 22a. These include an image processor module 24, a CPU module 26 and a memory module 28, known in the art as a frame buffer for storing image data arrays. The computer system 22 communicates with a separate system control 30 through a high speed serial link 32. The input device 14 can include a mouse, joystick, keyboard, track ball, touch activated screen, light wand, voice control, or any similar or equivalent input device, and may be used for interactive geometry prescription.

The system control 30 includes a set of modules connected together by a backplane 30a. These include a CPU module 34 and a pulse generator module 36 which connects to the operator console 12 through a serial link 38. It is through link 38 that the system control 30 receives commands from the operator to indicate the scan sequence that is to be performed. The pulse generator module 36 operates the system components to carry out the desired scan sequence and produces data which indicates the timing, strength and shape of the RF pulses produced, and the timing and length of the data acquisition window. The pulse generator module 36 connects to a set of gradient amplifiers 40, to indicate the timing and shape of the gradient pulses that are produced during the scan. The pulse generator module 36 can also receive patient data from a physiological acquisition controller 42 that receives signals from a number of different sensors connected to the patient, such as ECG signals from electrodes attached to the patient. And finally, the pulse generator module 36 connects to a scan room interface circuit 44 which receives signals from various sensors associated with the condition of the patient and the magnet system. It is also through the scan room interface circuit 44 that a patient positioning system 46 receives commands to move the patient to the desired position for the scan.

The gradient waveforms produced by the pulse generator module 36 are applied to the gradient amplifier system 40 having Gx, Gy, and Gz amplifiers. Each gradient amplifier excites a corresponding physical gradient coil in a gradient coil assembly generally designated 48 to produce the magnetic field gradients used for spatially encoding acquired signals. The gradient coil assembly 48 forms part of a magnet assembly 50 which includes a polarizing magnet 52 and a whole-body RF coil 54. A transceiver module 56 in the system control 30 produces pulses which are amplified by an RF amplifier 58 and coupled to the RF coil 54 by a transmit/receive switch 60. The resulting signals emitted by the excited nuclei in the patient may be sensed by the same RF coil 54 and coupled through the transmit/receive switch 60 to a pre-amplifier 62. The amplified MR signals are demodulated, filtered, and digitized in the receiver section of the transceiver 56. The transmit/receive switch 60 is controlled by a signal from the pulse generator module 36 to electrically connect the RF amplifier 58 to the coil 54 during the transmit mode and to connect the Pre-amplifier 62 to the coil 54 during the receive mode. The transmit/receive switch 60 can also enable a separate RF coil (for example, a surface coil) to be used in either the transmit or receive mode.

The MR signals picked up by the RF coil 54 are digitized by the transceiver module 56 and transferred to a memory module 64 in the system control 30. A scan is complete when an array of raw k-space data has been acquired in the memory module 64. This raw k-space data is rearranged into separate k-space data arrays for each image to be reconstructed, and each of these is input to an array processor 66 which operates to Fourier transform the data into an array of image data. This image data is conveyed through the serial link 32 to the computer system 22 where it is stored in memory. In response to commands received from the operator console 12, this image data may be archived in long term storage or it may be further processed by the image processor 24 and conveyed to the operator console 12 and presented on the display 18.

Memory module 28 and memory module 64 are tangible and non-transitory storage media such as magnetic drives, optical drives, or the like. It is contemplated that memory module 28 and/or memory module 64 include a set of instructions (e.g., a program) for carrying out embodiments of the invention. However, a portable and tangible storage device (not shown) could be used to store instructions for carrying out embodiments of the inventions.

It has been determined that navigator-based correction methods often assume that additional modulation present in center echoes (i.e., echoes covering the center or central region of k-space) is the same modulation as that predicted by the first few navigator echoes. It has also been determined that this assumption is often not accurate. For example, an additional linear phase term can build up across echoes as a result of back electromotive force due to mechanical resonance of the gradient coil. As a result, the modulation of the center echoes will often not be well corrected when only a navigator-based correction method is employed. In other words, navigator echoes do not always provide the proper phase correction term(s). As such, a drift of the Nyquist ghost can result.

Embodiments of the invention determine a plurality of phase correction coefficients that may be applied to EPI scan data to produce "corrected" EPI scan data. In other words, the phase correction coefficients can be employed to determine phase errors, which can be removed from EPI scan data to produce "corrected" EPI scan data. Accordingly, image artifacts are reduced when the "corrected" EPI scan data is employed during image reconstruction.

The phase correction coefficients can be employed to correct for various types of phase errors. For example, the phase correction coefficients can be used to correct for Nyquist ghost phase errors and $B_0$ field drift (i.e., center frequency drift) phase errors. Further, embodiments of the invention need not entirely rely on navigator echo data to determine phase errors.

Figure 2:
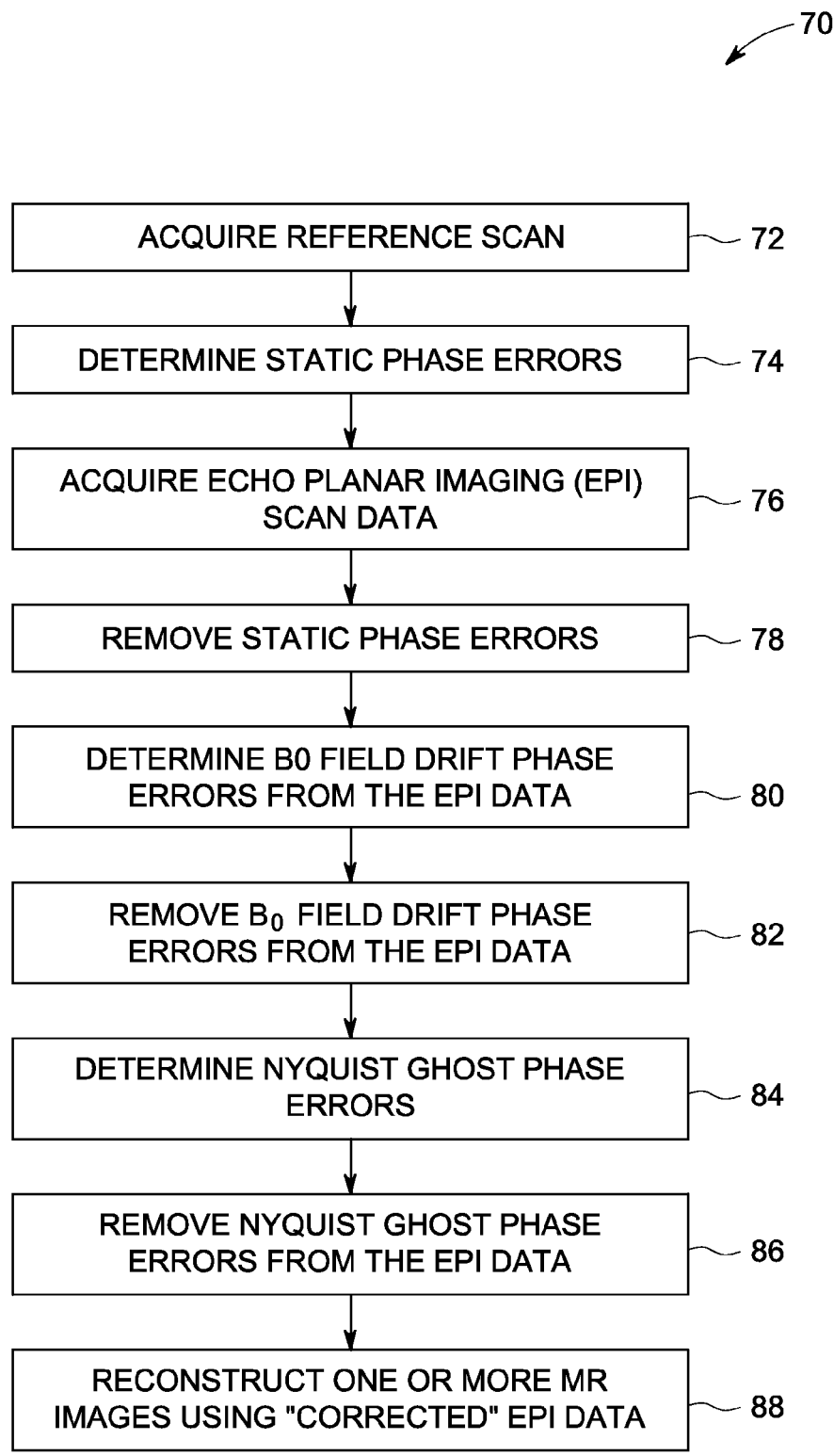
FIG. 2 is a flowchart of a technique for minimizing Nyquist ghost and the shifting of imaged object in dynamic EPI.

Referring to FIG. 2, a flowchart depicts a technique 70 for reducing artifacts in an EPI image. Starting at block 72, a reference scan is acquired. At block 74, static phase errors, $\varphi(x)$, are determined from the reference scan. At block 76, MR scan data that includes EPI data for a plurality of images is acquired. According to embodiments of the invention, the MR scan employed to elicit the MR scan data includes an EPI sequence. According to one embodiment of the invention, the MR scan is free of navigator echo pulses. However, according to another embodiment, the MR scan may include navigator echo pulses. That is, it is contemplated that navigator echo pulses may be intermixed with the EPI sequence. Further details regarding each embodiment will be set forth below.

At block 78, the static phase errors are removed from the EPI scan data. An embodiment illustrating the removal of static phase errors follows.

According to such an embodiment, while $\varphi(x)$ represents static phase difference between even and odd echoes, which can be determined from the reference scan, represents the per-temporal-frame additional phase difference (with t representing temporal frame or time), and $\theta(n,t)$ represents $B_0$ field drift. A phase correction equation that encompasses each type of phase error (i.e., $\varphi(x)$, $\phi(x,t)$, $\theta(n,t)$) can be formulated by denoting $\hat{d}(k_x,k_y,t)$ as the k-space EPI data acquired at time t. $k_x$ is the readout axis, and $k_y$ is the phase encoding axis. It is assumed that modulation between even and odd echoes is in the phase profile only (i.e., no magnitude modulation).

Taking an inverse Fourier transform on $\hat{d}(k_x,k_y,t)$ along $k_x$ yields time series data $d(x,k_y,t)$ in the hybrid $k_y$-x space. For formulation purposes, it is assumed that phase encoding is at $k_y = n\Delta k_y$, where $\Delta k_y$ is a Nyquist sampling spacing in the $k_y$ direction, $$n = -\frac{N}{2}, \left(-\frac{N}{2}+1\right), \ldots, \left(\frac{N}{2}-1\right),$$

and N is the number of phase encoding lines (assumed to be an even number).

Accordingly, $d(x,n\Delta k_y,t)$ can be written as follows:

$$d(x, n\Delta k_y, t) = \qquad (\text{Eqn. 1})$$

$$\begin{cases} d_{ideal}(x, n\Delta k_y, t)\exp\left[i\left(\frac{\varphi(x)}{2} + \frac{\phi(x,t)}{2} + \theta(n,t)\right)\right], & n \text{ even} \\ d_{ideal}(x, n\Delta k_y, t)\exp\left[i\left(\frac{-\varphi(x)}{2} + \frac{-\phi(x,t)}{2} + \theta(n,t)\right)\right], & n \text{ odd}, \end{cases}$$

where $d_{ideal}(k_x,k_y,t)$ is the "ideal" EPI data without any phase modulation.

Since $\theta(n,t)$ accounts for phase accumulation (i.e., phase errors) due to temperature related $B_0$ field drift relative to time 0 (i.e., $B_0$ field drift errors), the $\theta(n,t)$ term has the same sign for even and odd echoes and can be written in the following linear form:

$$\theta(n,t) = a(t)n + b(t), \qquad (\text{Eqn. 2}),$$

where a(t) and b(t) are temporal-frame dependent coefficients (i.e., a set of phase correction coefficients) to be determined.

With regard to $\phi(x,t)$ (i.e., per-temporal-frame phase difference), $\phi(x,t)$ accounts for the opposite phase modulation between even and odd echoes due to other changes of hardware states (e.g., short term eddy currents) and can be written, according to one embodiment, in a polynomial form:

$$\phi(x, t) = \sum_{q=0}^{Q} c_q(t)x^q, \qquad (\text{Eqn. 3})$$

where Q is the polynomial order and $c_q(t)$ is the qth polynomial coefficient at time t.

Note that both $\phi(x,t)$ and $\theta(n,t)$ describe quantities relative to time 0 and, therefore, $\Phi(x,0)=0$ and $\theta(n,0)=0$. Accordingly, the dynamic phase correction problem can be posed as the following: Given $\varphi(x)$ from the static reference data, find $\theta(n,t)$ and $\phi(x,t)$ in the form of Eqn. (2) and (3) based on the phase encoded scan data (i.e., EPI data), and remove them from the scan data to minimize the Nyquist ghost and $B_0$ field drift. Accordingly, navigator echo data need not be employed to determine phase errors $\phi(x,t)$ and $\theta(n,t)$. However, as explained above, it is contemplated that navigator echo data may be employed to determine $\theta(n,t)$.

Nonetheless, proceeding with the embodiment where navigator echo data is not employed, static phase modulation $\varphi(x)$ (determined from reference scan) can be removed from the EPI data at each time point. The resulting data, $d'(x,n\Delta k_y,t)$, can therefore be presented in the following form:

$$d'(x, n\Delta k_y, t) = \qquad (\text{Eqn. 4})$$

$$\begin{cases} d_{ideal}(x, n\Delta k_y, t)\exp\left[i\left(\frac{\phi(x,t)}{2} + \theta(n,t)\right)\right], & n \text{ even} \\ d_{ideal}(x, n\Delta k_y, t)\exp\left[i\left(\frac{-\phi(x,t)}{2} + \theta(n,t)\right)\right], & n \text{ odd}, \end{cases}$$

Accordingly, $d'(x,n\Delta k_y,t)$ represents EPI data having static phase errors, $\varphi(x)$, removed.

After removing static phase errors at block 78, $B_0$ field drift errors are determined at block 80. An embodiment illustrating the determination of the $B_0$ field drift errors, $\theta(n,t)$, follows.

Based on an assumption that there is negligible motion of the imaging object between time 0 and time t, the phase difference between $d_{ideal}(x,n\Delta k_y,t)$ and $d_{ideal}(x,n\Delta k_y,0)$ is negligible. Further, based on this assumption and that $\phi(x,0)=0$ and $\theta(n,0)=0$, the phase of $d'(x,n\Delta k_y,0)$ (i.e., the phase of the first temporal frame of MR data) equals the phase of $d_{ideal}(x,n\Delta k_y,t)$ can be subtracted from both sides of Eqn. 4.

As such, when we subtract the phase of $d'(x,n\Delta k_y,0)$ from $d'(x,n\Delta k_y,t)$, the resulting data set, $d''(x,n\Delta k_y,t)$, can be presented in the following form:

$$d''(x, n\Delta k_y, t) = \qquad (\text{Eqn. 5})$$

$$\begin{cases} |d_{ideal}(x, n\Delta k_y, t)| \cdot \exp\left[i\left(\frac{\phi(x,t)}{2} + \theta(n,t)\right)\right], & n \text{ even} \\ |d_{ideal}(x, n\Delta k_y, t)| \cdot \exp\left[i\left(\frac{-\phi(x,t)}{2} + \theta(n,t)\right)\right], & n \text{ odd}, \end{cases}$$

where |·| denotes a magnitude operator.

Based on Eqn. 5, the phase of d"(x,nΔk$_y$,t) can be used to estimate and θ(n,t). It is noted that that different "even" echoes have the same φ(x,t) term but a different θ(n,t) term. It is also noted that for a given even echo, θ(n,t) is constant along the x axis.

Accordingly, 1D magnitude-square-weighted polynomial fitting (e.g., a polynomial in the form of Eqn. 3) can be performed along the x axis for each even echo. Next, a magnitude-square-weighted linear fitting can be performed along the k$_y$ axis on the constant coefficients (i.e., zeroth order coefficient c$_0$(t)) obtained from the previous step to determine a(t) and b(t), thus determining θ(n,t).

According to the embodiment presented above, θ(n,t) is determined from the EPI data without the need to gather or rely on navigator echo data. According to another embodiment, however, navigator echo data may be gathered and used to determine the B$_0$ field drift errors, θ(n,t). According to such an embodiment, the MR scan employed at block 72 would also include navigator echo pulses. Accordingly, the navigator echo data gathered therefrom would be employed at block 80 to determine the B$_0$ field drift phase errors, θ(n,t).

Once θ(n,t) is determined, whether by relying on navigator echo data or by not relying on navigator echo data, θ(n,t) can be removed from the phase of all echoes of d"(x,nΔk$_y$,t) at block 82. In other words, B$_0$ field drift phase errors can be removed from the EPI data.

At block 84, Nyquist ghost phase errors, φ(x,t), can be determined or estimated. An embodiment illustrating the determination of Nyquist ghost phase errors φ(x,t) follows.

With respect to estimating φ(x,t), a data set, d'''(x,nΔk$_y$,t), can be constructed from d"(x,nΔk$_y$,t) after θ(n,t) is removed (i.e., block 82). To do so, according to one embodiment, the magnitude of d'''(x,nΔk$_y$,t) is obtained by taking the square root of the product of d"(x,nΔk$_y$,t) and d"(x,(n+1)Δk$_y$,t) (i.e., each neighboring even-odd echo pair), where:

$$n = -\frac{N}{2}, \left(-\frac{N}{2}+1\right), \ldots, \left(\frac{N}{2}-2\right). \quad \text{(Eqn. 6)}$$

The phase of d'''(x,nΔk$_y$,t) is set as the phase difference between d"(x,nΔk$_y$,t) and d"(x,(n+1)Δk$_y$,t). The phase difference is negated when n is an odd number to obtain a positive sign in the φ(x,t) term. Mathematically, d'''(k$_x$,nΔk$_y$,t) can take on following form:

$$d'''(x, n\Delta k_y, t) = \quad \text{(Eqn. 7)}$$
$$\sqrt{|d_{ideal}(x, n\Delta k_y, t)d_{ideal}(x, (n+1)\Delta k_y, t)|} \cdot \exp[i\phi(x, t)],$$
$$n = -\frac{N}{2}, \left(-\frac{N}{2}+1\right), \ldots, \left(\frac{N}{2}-2\right).$$

Fitting the phase of the (N−1) echoes of d'''(k$_x$,nΔk$_y$,t) with a single 1D polynomial (weighted by the squared magnitude) along the x axis yields the polynomial coefficients c$_q$(t) in Eqn. 3, where q=0, 1, . . . , Q, thus determining or estimating φ(x,t).

Accordingly, at block 86, using φ(x,t), Nyquist ghost errors can be removed from the EPI data. Accordingly, a "corrected" EPI data set is produced, where static phase errors, φ(x), B$_0$ field drift phase errors, θ(n,t), and Nyquist ghost errors, φ(x,t) are removed or at least minimized.

Once the "corrected" EPI data set is produced, one or more MR images at the current temporal frame can be reconstructed at block 88 using the "corrected" EPI data. Note that MR images at each temporal frame are reconstructed using the same flowchart shown in FIG. 2.

It is noted that, according to one embodiment, a temporally-smoothed version of θ(n,t) and φ(x,t) can be removed from d'(x,nΔk$_y$,t), for which the static phase errors φ(x) are already removed, at each time point to minimize the Nyquist ghost and B$_0$ field drift.

Further, it is also noted that the determination and removal of static phase errors φ(x) need not occur before determination of the B$_0$ field drift phase errors (block 80). Rather, according to an embodiment, the static phase errors may be determined and/or removed from the EPI data after the B$_0$ field drift phase errors are determined or removed or even after the Nyquist ghost errors are determined or removed.

Blocks 76-88 of technique 70 produce one image per slice at a single time point. According to embodiments of the invention, blocks 76-88 are repeated for different time points.

While the invention is described for 2D EPI, all the analysis and algorithm can also apply to the 3D echo volume imaging (EVI) cases with trivial modification of the phase encoding in k$_y$ to phase encoding in both k$_y$ and k$_z$. Determining φ(x) and φ(x,t) are identical to what has been described above to determine θ(n,t), instead of linear fitting along k$_y$, one linear fits along both k$_y$ and k$_z$ according to the visiting order in (k$_y$,k$_z$) plane.

Embodiments of the invention provide for a computer implemented apparatus and method of removing phase errors from an MR image.

Therefore, according to one embodiment of the invention, a magnetic resonance imaging (MRI) apparatus includes an MRI system having a plurality of gradient coils positioned about a bore of a magnet, and a radio-frequency (RF) transceiver system and an RF switch controlled by a pulse module to transmit RF signals to an RF coil assembly to acquire MR images. The MRI apparatus also includes a computer programmed to implement a scan sequence configured to elicit scan data, wherein the scan sequence comprises an echo planar imaging (EPI) sequence configured to elicit the image data and to acquire the scan data. The computer is also programmed to manipulate the scan data to determine a first plurality of phase errors in the image data responsible for a Nyquist ghost, wherein the manipulated scan data is free of navigator echo data, remove the first plurality of phase errors from the image data, and reconstruct an image based on the image data having the first plurality of phase errors removed therefrom.

According to another embodiment of the invention, a method a method of magnetic resonance (MR) imaging includes acquiring MR data with at least one MR coil, wherein the MR data comprises echo planar imaging (EPI) data and determining a first set of coefficients for phase correction from the EPI data, wherein determining the first set of coefficients does not rely on navigator echo data. The method also includes employing the first set of coefficients to remove Nyquist ghosting phase errors in the EPI data and reconstructing a plurality of images from the EPI data having the Nyquist ghosting phase errors removed therefrom.

According to another embodiment of the invention, a computer readable storage medium having a sequence of instructions stored thereon, which, when executed by a computer, causes the computer to initiate a magnetic resonance (MR) scan that employs an echo planar imaging (EPI) sequence configured to elicit imaging data and to determine a first set of phase correction coefficients from the imaging data, wherein the determination of the first set of phase correction coefficients does not rely on navigator echo data. The instructions also cause the computer to employ the first set of phase correction coefficients to remove a first set of phase errors from the imaging data responsible for Nyquist ghosting and to reconstruct at least one image from the imaging data having the first set of phase errors removed.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A magnetic resonance imaging (MRI) apparatus comprising:
    an MRI system having a plurality of gradient coils positioned about a bore of a magnet, and a radio-frequency (RF) transceiver system and an RF switch controlled by a pulse module to transmit RF signals to an RF coil assembly to acquire MR images; and
    a computer programmed to:
        implement a scan sequence configured to elicit scan data, wherein the scan sequence comprises an echo planar imaging (EPI) sequence configured to elicit the image data;
        acquire the scan data;
        manipulate the scan data to determine a first plurality of phase errors in the image data responsible for a Nyquist ghost, wherein the manipulated scan data is free of navigator echo data;
        remove the first plurality of phase errors from the image data; and
        reconstruct an image based on the image data having the first plurality of phase errors removed therefrom.

2. The MRI apparatus of claim 1 wherein the computer, in being programmed to manipulate the scan data to determine the first plurality of phase errors, is programmed to manipulate the scan data to determine the first plurality of phase errors based on:

$$d(x, n\Delta k_y, t) = \begin{cases} d_{ideal}(x, n\Delta k_y, t)\exp\left[i\left(\frac{\varphi(x)}{2} + \frac{\phi(x,t)}{2} + \theta(n,t)\right)\right], & n \text{ even} \\ d_{ideal}(x, n\Delta k_y, t)\exp\left[i\left(\frac{-\varphi(x)}{2} + \frac{-\phi(x,t)}{2} + \theta(n,t)\right)\right], & n \text{ odd}, \end{cases}$$

wherein $d(x,n\Delta k_y,t)$ represents a time series data in the hybrid $k_y$-x space, $\phi(x,t)$ represents the first plurality of phase errors, $\theta(n,t)$ represents a second plurality of phase errors responsible for $B_0$ field drift, $\varphi(x)$ represents a third plurality of phase errors, and $d_{ideal}(x,n\Delta k_y, t)$ represents EPI data free of phase errors.

3. The MRI apparatus of claim 2 wherein $\theta(n,t)$ has the following form:

$$\theta(n,t)=a(t)n+b(t),$$

where a(t) and b(t) are temporal-frame dependent coefficients.

4. The MRI apparatus of claim 2 wherein $\phi(x,t)$ has the following form:

$$\phi(x, t) = \sum_{q=0}^{Q} c_q(t)x^q,$$

where Q is the polynomial order and $c_q(t)$ is a qth polynomial coefficient at time t.

5. The MRI apparatus of claim 1 wherein the scan sequence is free of navigator echo pulses.

6. The MRI apparatus of claim 5 wherein the computer is further programmed to:
    manipulate the image data to determine a second plurality of phase errors caused by $B_0$ field drift; and
    remove the second plurality of phase errors from the image data, wherein reconstruction of the image is further based on the image data having the second plurality of phase errors removed therefrom.

7. The MRI apparatus of claim 6 wherein the computer is further programmed to:
    implement a reference scan sequence prior to implementation of the scan sequence configured to elicit the scan data, wherein the reference scan sequence is free of phase encoding;
    acquire reference scan data elicited by the reference scan sequence;
    determine a third plurality of phase errors from the reference scan data; and
    remove the third plurality of phase scan errors from the image data prior to reconstruction of the image.

8. The MRI apparatus of claim 1 wherein the scan sequence further comprises a plurality of navigator echo pulses employed to acquire non-phased-encoded data.

9. The MRI apparatus of claim 8 wherein the computer is further programmed to:
    determine a second plurality of phase errors caused by $B_0$ field drift, wherein the determination of the second plurality of phase errors is based on the non-phased-encoded data; and
    remove the second plurality of phase errors from the image data, wherein reconstruction of the image is further based on the image data having the second plurality of phase errors removed therefrom.

10. The MRI apparatus of claim 9 wherein the computer is further programmed to temporally smooth the first and second plurality of phase errors prior to removing the first and second plurality of phase errors from the image data.

11. A method of magnetic resonance (MR) imaging comprising:
    acquiring MR data with at least one MR coil, wherein the MR data comprises echo planar imaging (EPI) data;
    determining a first set of coefficients for phase correction from the EPI data, wherein determining the first set of coefficients does not rely on navigator echo data;
    employing the first set of coefficients to remove Nyquist ghosting phase errors in the EPI data; and
    reconstructing a plurality of images from the EPI data having the Nyquist ghosting phase errors removed therefrom.

12. The method of claim 11 further comprising:
    implementing a MR scan to elicit the MR data, wherein the MR scan comprises an EPI sequence to elicit the EPI data and is free of navigator echo pulses;

determining a second set of coefficients from the EPI data; and employing the second set of coefficients to remove $B_0$ field drift phase errors in the EPI data such that $B_0$ field drift is minimized in the plurality of images.

13. The method of claim 11 further comprising:

implementing a MR scan to elicit the MR data, wherein the MR scan comprises an EPI sequence to elicit the EPI data and at least one navigator echo pulse;

determining a second set of coefficients from the EPI data and navigator echo data, wherein the navigator echo data is elicited by the at least one navigator echo pulse; and employing the second set of coefficients to minimize $B_0$ field drift in the plurality of images.

14. The method of claim 11 further comprising:

implementing a static reference scan free of phase encoding prior to implementing the MR scan; and determining phase errors in the EPI data based on the EPI data and static reference scan data, wherein the reference scan data is elicited by the static reference scan.

15. A computer readable storage medium having a sequence of instructions stored thereon, which, when executed by a computer, causes the computer to:

initiate a magnetic resonance (MR) scan that employs an echo planar imaging (EPI) sequence configured to elicit imaging data;

determine a first set of phase correction coefficients from the imaging data, wherein the determination of the first set of phase correction coefficients does not rely on navigator echo data;

employ the first set of phase correction coefficients to remove a first set of phase errors from the imaging data responsible for Nyquist ghosting; and reconstruct at least one image from the imaging data having the first set of phase errors removed.

16. The computer readable storage medium of claim 15 wherein the instructions that cause the computer to determine a first set of phase correction coefficients cause the computer to determine the first set of phase correction coefficients based on fitting echo data elicited by the EPI sequence to a polynomial.

17. The computer readable storage medium of claim 15 wherein the MR scan is free of navigator echo pulses.

18. The computer readable storage medium of claim 17 wherein the instructions further cause the computer to:

determine a second set of phase correction coefficients from the imaging data; and employ the first set of phase correction coefficients to remove a second set of phase errors responsible for $B_0$ field drift.

19. The computer readable storage medium of claim 15 wherein the MR scan employs navigator echo pulses to elicit navigator echo data.

20. The computer readable storage medium of claim 19 wherein the instructions further cause the computer to:

determine a second set of phase correction coefficients from the imaging data and the navigator echo data; and employ the second set of phase correction coefficients to remove a second set of phase errors responsible for $B_0$ field drift.

* * * * *

UNITED STATES PATENT AND TRADEMARK OFFICE
CERTIFICATE OF CORRECTION

PATENT NO.        : 8,483,457 B2                                Page 1 of 1
APPLICATION NO.   : 12/831562
DATED             : July 9, 2013
INVENTOR(S)       : Hinks et al.

It is certified that error appears in the above-identified patent and that said Letters Patent is hereby corrected as shown below:

In the Specifications

Col. 5, line 36, after "scan," insert
  -- $\phi(x,t)$ --; and

Col. 7, line 2, after "estimate" insert
  -- $\phi(x,t)$ --; and

In the Claims

Col. 9, line 59 (Claim 2), delete "$\phi(x)$" and
  substitute therefore -- $\varphi(x)$ --.

Signed and Sealed this
Twenty-eighth Day of January, 2014

Michelle K. Lee
*Deputy Director of the United States Patent and Trademark Office*